United States Patent [19]
Schack et al.

[11] Patent Number: 4,508,662
[45] Date of Patent: Apr. 2, 1985

[54] PENTAFLUOROTELLURIUMOXIDE FLUOROCARBONS

[75] Inventors: Carl J. Schack, Chatsworth; Karl O. Christe, Calabasas, both of Calif.

[73] Assignee: The United States of America as represented by the Secretary of the Air Force, Washington, D.C.

[21] Appl. No.: 478,589

[22] Filed: Mar. 24, 1983

[51] Int. Cl.$^3$ ............................................ C07C 165/00
[52] U.S. Cl. .................................... 260/550; 252/48.8
[58] Field of Search ........................................ 260/550

[56] References Cited
U.S. PATENT DOCUMENTS 4,216,338  8/1980  Schack et al. ...................... 560/227
4,222,968  9/1980  Schack et al. ...................... 260/653
4,329,330  5/1982  Christe et al. ...................... 423/473

OTHER PUBLICATIONS

Schack et al., Chem. Abstracts, vol. 93, (1980), p. 673, abstr. 249259n.
J. Smith et al., Inorg. Chem., (1970), 9 (6), 1442–1445.
S. Williamson et al., Inorg. Chem., 1, 673–677, (1962).
L. Anderson et al., J. Org. Chem., (1970), 35 (11), 3730–3733.
J. Fluorine Chem., 7, 192, 193, 195 (1973).
Mathers et al., Inorg. Syn., 3, 145 (1950).
Seppelt et al., Inorg. Chem., 12, 2727–2730 (1973).
Christe et al., Inorg. Chem., 20, 2104–2114 (1981).
Dudley et al., J. Am. Chem. Soc., 78, 290–292 (1956).

Primary Examiner—Donald G. Daus
Assistant Examiner—William A. Teoli, Jr.
Attorney, Agent, or Firm—Donald J. Singer; William J. O'Brien

[57] ABSTRACT

Pentafluorotellurium hypofluorite and pentafluorotellurium hypochlorite have been reacted with olefinic reactants to form fluorocarbon adducts containing the oxypentafluorotellurium group (TeF$_5$O—).

15 Claims, No Drawings

PENTAFLUOROTELLURIUMOXIDE FLUOROCARBONS

STATEMENT OF GOVERNMENT INTEREST

The invention described herein may be manufactured and used by or for the Government for governmental purposes without the payment of any royalty thereon.

BACKGROUND OF THE INVENTION

This invention relates to a method for synthesizing fluorocarbon fluids containing oxypentafluorotellurium (TeF$_5$O—) substituents. The TeF$_5$O— group is inherently dense and when incorporated into fluorocarbon fluids it provides enhanced density to those materials. In addition, the ether-like oxygen link furnishes molecular flexibility, lessening of steric hindrances, and retention of fluid properties.

These fluids find particular utility as agents for a wide variety of industrial applications requiring the utilization of highly dense fluids. They are especially useful as flotation agents for gyroscopes, compasses and other like instruments which must be dampened to minimize excessive vibration and oscillation problems.

To the best of our knowledge, no previous examples have been reported in the literature incorporating the TeF$_5$O— groups into fluorocarbons. Compounds containing the analogous sulfur substituent, SF$_5$OR$_f$, are known, being mainly obtained by reactions of SF$_5$OCl and SF$_5$OF with olefins. This work showed that the addition of SF$_5$OX to olefins proceeded according to the general equation:

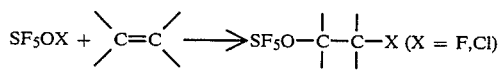  (I)

For both of these hypohalites, good yields of the adducts are often obtained but the hypofluorite reactions are sometimes difficult to control and much lower yields are realized. This is not surprising in view of the fact that CF$_3$OF reacts explosively with some olefins and its addition to them is superseded by fluorination reactions.

In the case of SeF$_5$OF reactions with olefins such as CF$_2$=CF$_2$, CF$_3$CF=CF$_2$ and CH$_2$=CH$_2$, no products containing the SeF$_5$O— group were identified. With perfluorocyclopentene a good yield of the adduct, SeF$_5$OC$_5$F$_9$, was obtained. No examples of the addition of SeF$_5$OCl to olefin have been reported.

Based on the observed trends in the reactivity of the Group VI hypofluorites with respect to olefins, one would expect that TeF$_5$OX, where X is F or Cl, should not undergo a facile addition reaction. Therefore, it was unexpected that the recently discovered TeF$_5$OF would react smoothly with olefins to provide TeF$_5$O— substituted fluorocarbons in high yield by addition across the olefin double bond. Furthermore, it has been found that TeF$_5$OCl also adds to olefins. In this instance, the reaction is more difficult to control to achieve the desired addition, and yields of the adducts are lower. All of the TeF$_5$O— substituted fluorocarbons are thermally stable fluids. Their either-like structure provides the desirable fluid properties exhibited by that class of compounds. In addition, they have enhanced density due to the presence of the TeF$_5$O— group.

SUMMARY OF THE INVENTION

In accordance with this invention, a novel class of high density fluids based on TeF$_5$O— substituted fluorocarbons and a process for their synthesis have been discovered. The synthesis utilizes oxypentafluorotellurium hypohalites as reactants to effect an addition reaction with aliphatic or alicyclic halogen substituted olefins to produce useful fluorocarbons substituted with the TeF$_5$O— group. The synthesis involves condensing the oxypentafluorotellurium hypohalite and an olefin together at subambient temperature, and allowing the mixture to gradually warm to ambient temperature. After a day, or longer if desired, the products are separated by fractional condensation. The following general equation describes this addition reaction.

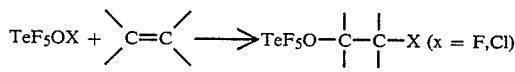  (II)

Yields of the adduct of this reaction are 60–86% in the case of the hypofluorite and 22–30% in the case of the hypochlorite.

Accordingly, the primary object of the invention is to provide a method for synthesizing novel high density halogen substituted hydrocarbon fluids.

Another object of this invention is to provide a method for synthesizing high density fluorocarbon fluids that utilizes pentafluorotellurium hypofluorite as a reactant.

Still another object of this invention is to provide a method for synthesizing halogen substituted hydrocarbons containing oxypentafluorotellurium substituents.

A further object of this invention is to provide a novel class of pentafluorotellurium oxide fluorocarbons.

The above and still further objects and advantages of the present invention will become more readily apparent upon consideration of the following detailed description thereof.

DESCRIPTION OF THE PREFERRED EMBODIMENT

Pursuant to the above-defined objects, the present invention concerns itself with a novel method for synthesizing pentafluorotellurium oxide fluorocarbons and to the novel high density fluids prepared thereby. The invention is brought into effect by accomplishing an addition reaction at subambient temperatures between a pentafluorotellurium hypohalite, such as pentafluorotellurium hypofluorite or pentafluorotellurium hypochlorite, and an appropriate halogen substituted, aliphatic or alicyclic, hydrocarbon olefin. The resulting fluids are highly dense, thermally stable and contain oxypentafluorotellurium (TeF$_5$O—) as a substituent on the fluorocarbon chain. Such highly dense fluids are especially desired as flotation agents in improved gyroscopes.

The reaction for synthesizing the novel fluorocarbon fluids of this invention is illustrated by the following equation.

  (II)

wherein X is F or Cl and $R_f$ is the radical $-CF_2CF_3$; $-CF_2CF_2Cl$; $-CFClCF_3$; $-CF_2CF_2CF_3$; $-CF(CF_3)_2$; $-CF_2CFClCF_3$; or

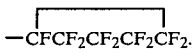
$-CFCF_2CF_2CF_2CF_2$.

This novel reaction represents a new route to the preparation of halocarbons containing $TeF_5O-$ substituents. The hypohalite reactant and the olefinic reactant are cocondensed at subambient temperatures and then allowed to gradually warm up to ambient temperature. The reaction mixture is then maintained at ambient temperature for at least a 24 hour period and then the resulting reaction products are separated by fractional condensation.

The volatile materials used in the reaction scheme of this invention were manipulated in a stainless steel vacuum line equipped with Teflon FEP U-traps, 316 stainless steel bellows-seal valves, and a Heise Bourdon tube-type gauge. The synthetic reactions employed here were usually conducted in stainless steel cylinders. Infrared spectra were recorded on a Perkin Elmer Model 283 spectrophotometer using cells equipped with AgCl, AgBr, or CsI windows. The $^{19}F$ NMR spectra were recorded at 84.6 MHz on a Varian Model EM 390 spectrometer with internal $CFCl_3$ as a standard with a negative chemical shift being upfield from $CFCl_3$.

The $TeF_5OF$ employed herein was prepared from $Cs^+TeF_5O^-$ and $FOSO_2F$ by reaction at $-45°$ C. as shown in Example 1 which follows. The $TeF_5OCl$ was prepared by reacting $TeF_5OH$ and $ClOSO_2F$ at temperatures below and up to ambient in accordance with the procedure described in J. Fluorine Chem. 1982, 21, 393.

The reaction scheme for synthesizing the $TeF_5OF$ reactant used in the method of this invention is further illustrated with greater specificity by Example I which follows.

EXAMPLE I

A 30 ml stainless steel Hoke cylinder was loaded with $CsTeF_5O$ (3.42 mmol) in the glove box. After evacuation and cooling of the cylinder to $-196°$ C., $FOSO_2F$ (2.79 mmol) was added from the vacuum line. The closed cylinder was slowly warmed to $-78°$ C. in a liquid nitrogen-$CO_2$ slush bath and finally kept at $-45°$ C. for 9d. Upon recooling to $-196°$ C. about 4-5 $cm^3$ noncondensable gas was observed to be present. This was pumped away and the condensable products were separated by fractional condensation in a series of U-traps cooled at $-78°$, $-126°$, and $-196°$ C. The $-78°$ C. fraction was $TeF_5OH$ (0.19 mmol) while the $-196°$ C. fraction was $TeF_6$ (0.49 mmol).

A white solid was retained at $-126°$ C. which changed to a colorless glass and melted, over a range of a few degrees, near $-80°$ C. to a clear, colorless liquid. This material was identified as $TeF_5OF$ (1.91 mmol, 68% yield) based on its vapor density molecular weight; found, 256.2; calc., 257.6 g/mol. Further identification was based on its spectroscopic properties and on the preparation of derivatives. The observed weight loss of the solid (0.375 g) agreed well with that calculated (0.389 g) for the conversion of 2.79 mmol $CsTeF_5O$ to $CsSO_3F$. Vapor pressure-temperature data of $TeF_5OF$ were measured: T°C., Pmm; $-79.3$, 16; $-64.2$, 45, $-57.6$, 63; $-46.9$, 108; $-32.5$, 210; $-23.0,312$.

The $TeF_5OF$ compound of Example 1 is colorless as a gas and liquid. Its vapor pressure-temperature relationship for the range $-79°$ to $-23°$ C. is given by the equation,.

$$\log P_{mm} = 6.9022 - 1101.2/T°K.$$

The extrapolated boiling point is 0.6° C. The derived heat or vaporization is $\Delta H_{vap} = 5039$ cal $mol^{-1}$ and the Trouton constant is 19.4 indicating little or no association in the liquid phase. Vapor density measurements showed that in the gas phase the compound is also not associated. A sharp melting point for $TeF_5OF$ was not observed because the samples showed a tendency to form a glass near $-80°$ C. The compound appears to be completely stable at ambient temperature and has been stored in stainless steel cylinders for more than four months without any sign of decomposition. Examples 2 to 7, which follow, disclose in detail the reaction scheme and the resulting high density fluids illustrated by equation (II) above.

EXAMPLE 2

A 10 ml cylinder was evacuated, cooled to $-196°$ C., and then successively $TeF_5OF$ (1.42 mmol) and $C_2F_4$ (2.30 mmol) were condensed into it. The closed cylinder was allowed to warm slowly in a dewar containing solid carbon dioxide cooled to $-196°$ C. After warm up, the reactor was kept at ambient temperature for a day. The products were separated by fractional condensation through a series of connected U-traps cooled to $-112°$ and $-196°$ C. The more volatile material collected at $-196°$ C. was mainly unreacted $C_2F_4$ together with $TeF_6$. The latter is both a common contaminant of $TeF_5OF$ and a degradation product thereof. Retained in the trap at $-112°$ was $TeF_5OCF_2CF_3$ (0.85 mmol. 60% yield). This material was a clear, colorless liquid and had a vapor pressure of about 4 mm of Hg at $-78°$ C. and had a measured vapor density of 355.2 g/mol (theory for $TeF_5OC_2F_5$ is 357.6 g/mol). Storage at ambient temperature or heating for a day to 95° C. in stainless steel vessels did not result in any detectable decomposition.

Further identification was based on its spectroscopic properties. The $^{19}F$ NMR spectrum was that expected for an $AB_4$ spin system ($TeF_5O-$ possesses one apical and four equatorial fluorines) and an alkyl fluorocarbon. Observed NMR parameters were [ppm(multiplicity)] where b-broad, c-complex, d-doublet, t-triplet, qi-quintet, s-sextet, and m-multiplet. For $F^ATeF_4$-$^BOCF_2{}^XCF_3{}^Y$: A-49.7, B-40.0 (t of $B_4$), X-80.2 (cm), Y-87.4(t); $J_{AB}=185$, $J_{BX}=5.5$, $J_{XY}2.3$ Hz. The measured area ratios for these four types of fluorine were in the anticipated ratio of 1:4:2:3. Infrared bands noted were $cm^{-1}$ (intensity): 1247(vs), 1190(vs), 1110(vs), 745(vs), 722(s), and 328(s). The position and intensity of the three bands at about 745,722, and 325 $cm^{-1}$ are very characteristic of stretching and bending vibrations of the $TeF_5$ group.

EXAMPLE 3

A 10 ml cylinder was loaded as above with $TeF_5OF$(0.65 mmol) and perfluoropropene (0.81 mmol). After slowly warming from $-196°$ C. to ambient temperature the reactor was kept at ambient temperature for 2 days. Fractional condensation through U-traps cooled at $-78°$, $-95°$, and $-196°$ C. was used to separate the products. The $-95°$ C. trap contained $TeF_5OC_3F_7$ (0.51 mmol, 78% yield) which was a clear, colorless liquid and had a vapor density of 404 g/mol (theory=407.6 g/mol). Storage at ambient temperature or heating for a day at 95° C. in stainless steel vessels did not result in any detectable decomposition.

Further identification was based on spectroscopic properties. The $^{19}$F NMR spectrum revealed that the product was a mixture of isomers as shown in the equation.

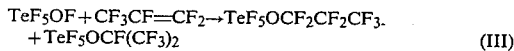

$\text{TeF}_5\text{OF} + \text{CF}_3\text{CF}=\text{CF}_2 \rightarrow \text{TeF}_5\text{OCF}_2\text{CF}_2\text{CF}_3$
$+ \text{TeF}_5\text{OCF}(\text{CF}_3)_2$ (III)

These two isomers are the result of a non-regiospecific addition of TeF$_5$O— and F— to the olefin double bond. Based on the NMR spectrum, the ratio of the n-propyl to the iso-propyl derivative was 70:30. Again the AB$_4$ patterns, characteristic for the TeF$_5$O— groups were observed. The NMR parameters were ppm(multiplicity) for $F^A\text{TeF}_4{}^B\text{OCF}_2{}^X\text{CF}_2{}^Y\text{CF}_3{}^Z$: A-53.9, B-42.6 (t of B$_4$), X-76.6(cm), Y-132.8(t,m), Z-84,6(t); $J_{AB}=180$, $J_{BX}=5.4$, $J_{XY}=0.9$, $J_{YZ}=8.1$ Hz. The correct data ratios for these assignments (1:4:2:2:3) was observed. For $F^A\text{TeF}_4{}^B\text{OCF}^X(\text{CF}_3)_2{}^Y$: A-53.4, B-41.8(bB$_4$), X-132.7(bqi), Y-84.3(s); $J_{AB}=185$, $J_{BX}=11$, $J_{XY}=2.2$, $J_{BY}=2.2$ Hz and the measured area ratios were respectively 1:4:1:6 in agreement with those expected for this isomer.

An infrared spectrum of the mixture showed bands at cm$^{-1}$(int.): 1350(w), 1320(m), 1300(w), 1265(sh), 1245(vs), 1210(m), 1180(sh), 1170(s), 1145(s), 1005(s), 754(s), 723(s), and 322(s). Bands typical of the TeF$_5$ group are prominent and confirm its presence in this material.

EXAMPLE 4

As in the preceeding examples TeF$_5$OF(1.65 mmol) and perfluorocyclopentene (1.78 mmol) were reacted in a stainless steel cylinder. Fractional condensation resulted in retention of TeF$_5$OC$_5$F$_9$ (1.42 mmol, 86% yield) in a trap cooled at −78° C. This material was a colorless liquid with a vapor pressure of about 24 mm Hg at 20° C. and a vapor density of 467 g/mol (theory=469.6 g/mol). It exhibited the same good storability and thermal stability of the other TeF$_5$OR$_f$ examples.

The $^{19}$F NMR for TeF$_5$OC$_5$F$_9$ showed the typical AB$_4$ pattern for the TeF$_5$ group and a very complex multiplet, expected for a cyclic C$_5$ compound; [ppm (multiplicity)] $F^A\text{TeF}_4{}^B\text{OC}_5\text{F}_9{}^X$: A-50.7, B-40.0(m), X-131(m). The area ratio for the three types of fluorine were as expected (1:4:9). Infrared bands for TeF$_5$OC$_5$F$_9$ were at cm$^{-1}$(int.); 1320(s), 1280(m), 1224(vs), 1166(s), 988(vs), 744(vs), 711(s), and 319(s) and are in agreement with the above formulation. The synthesis of the product of this example is illustrated by the following equation:

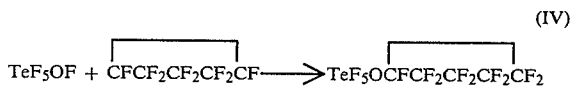

(IV)

EXAMPLE 5

As in the preceeding examples, TeF$_5$OF(0.41 mmol) and chlorotrifluoroethylene (0.47 mmol) were reacted. On workup an adduct of the empirical formula TeF$_5$OC$_2$F$_4$Cl was retained in a trap cooled at −112° C. (0.27 mmol). This adduct was stable and storable in the same way as the preceeding examples.

The $^{19}$F NMR spectrum of this product revealed the presence of two isomers resulting from the non-regiospecific addition of TeF$_5$OF as shown in the following equation.

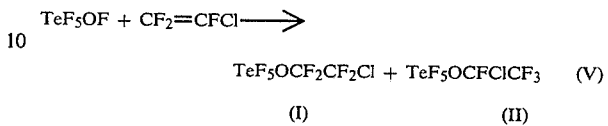

$\text{TeF}_5\text{OF} + \text{CF}_2=\text{CFCl} \longrightarrow$ $\text{TeF}_5\text{OCF}_2\text{CF}_2\text{Cl} + \text{TeF}_5\text{OCFClCF}_3$ (V)

(I) (II)

The ratio of I to II in the mixture was 40:60 indicating that steric factors were not governing the direction of the addition since the more hindered isomer was formed in a larger percentage. Measured NMR parameters were [ppm (multiplicity)] $F^A\text{TeF}_4{}^B\text{OCF}_2{}^X\text{CF}_2{}^Y\text{Cl}$: A-49.5, B-40.2 (t of B$_4$), X-78.0(qi,t), Y-73.1(t): $J_{AB}179$, $J_{BX}5.3$, $J_{XY}1.45$ Hz. The correct area ratios (1:4:2:2) for this assignment were observed. For $F^A\text{TeF}_4{}^B\text{OCF}^X\text{ClCF}_3{}^Y$: A-49.0, B-38.3(d of B$_4$), X-69.5(qi,q), Y-85.8(d); $J_{AB}180$, $J_{BX}6.6$, $J_{XY}1.7$ Hz were measured with the correct area ratios of 1:4:1:3.

From the known infrared spectrum of pure TeF$_5$OCF$_2$CF$_2$Cl prepared as in Example 5, the infrared spectrum of TeF$_5$OCFClCF$_3$ in the above isomer mixture was obtained by difference, cm$^{-1}$(int.): 1320(s), 1245(vs), 1130(s), 1105(vs), 968(s), 743(s), 708(m), and 322(s). Again the last three bands are indicative of the presence of a TeF$_5$ group in the molecule.

EXAMPLE 6

A 30 ml cylinder was loaded at −196° C. with TeF$_5$OCl (2.58 mmol) and tetrafluoroethylene (3.07 mmol) and allowed to warm slowly to ambient temperature overnight. Pumping on the reactor at that time through traps cooled at −78°, −112°, and −196° C. resulted in the isolation of TeF$_5$OCF$_2$CF$_2$Cl in the −112° C. trap (0.78 mmol, 30% yield) with a measured vapor density of 372 g/mol (theory=374 g/mol). This clear, colorless liquid was stable and unchanged after heating for 16 hours at 95° C. and was storable in stainless steel.

The $^{19}$F NMR spectrum of the product showed it to be the expected adduct with the measured parameters being identical to those noted for this compound in its isomer mixture with TeF$_5$OCFClCF$_3$ as described in Example 4. Infrared bands for the pure TeF$_5$OCF$_2$CF$_2$Cl obtained by this reaction were at cm$^{-1}$(int.): 1310(w), 1198(vs), 1182(vs), 1128(s), 981(s), 743(s), 724(s), and 324 (ms). The presence of the TeF$_5$ group is apparent from the last three observed bands which are characteristic for that group.

The main products from this reaction were CF$_3$CF$_2$Cl which was trapped at −196° C. and a nonvolatile, colorless oily liquid which remained in the reaction cylinder. This oily liquid was assumed to be (TeF$_4$O)$_2$. Both it and the CF$_3$CF$_2$Cl arose from the following reaction.

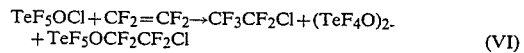

$\text{TeF}_5\text{OCl} + \text{CF}_2=\text{CF}_2 \rightarrow \text{CF}_3\text{CF}_2\text{Cl} + (\text{TeF}_4\text{O})_2$
$+ \text{TeF}_5\text{OCF}_2\text{CF}_2\text{Cl}$ (VI)

Because of the great difference in volatility between these materials, the desired TeF$_5$OCF$_2$CF$_2$Cl adduct was easily separated out of the reaction mixture.

EXAMPLE 7

A sample of perfluoropropene (2.78 mmol) was cooled at −95° C. in a Teflon FEP U-trap on the vacuum line. From a reservoir at ambient temperature, TeF$_5$OCl (2.59 mmol) was slowly bled into the trap containing the cold C$_3$F$_6$. This addition was monitored by reading the pressure in the reservoir and in 2 hours the stated amount was added. The mixture was left at −78° C. overnight and the products were separated by fractional condensation in U-traps cooled at −78°, −95°, and −196° C. Collected at −95° C. was TeF$_5$OCF$_2$CFClCF$_3$(0.57 mmol, 22% yield), a clear, colorless liquid with a vapor density of 426 g/mol (theory=424 g/mol). This compound was stable at 95° C. and storable at ambient temperature for long periods as noted for the other TeF$_5$OR$_f$ materials.

Further identification based on $^{19}$F NMR measurements confirmed the composition of this product. Observed parameters were [ppm (multiplicity)] F$^A$TeF$_4$-$^B$OCF$_2^X$CF$^Y$ClCF$_3^Z$: A-49.7, B-39.9(t of B$_4$), X-71.7(cm), Y-139.7(s), Z-79.2(t,d); J$_{AB}$185, J$_{BX}$5.4, J$_{XY}$6.7, J$_{YZ}$6.7, J$_{XZ}$9.5 Hz. Area ratios for the various fluorine resonances (1:4:2:1:3) agreed with assignments. Infrared bands for this compound were at cm$^{-1}$(int.): 1297(ms), 1268(s), 1242(vs), 1177(s), 1136(ms), 987(s), 973(s), 744(s), 721(s), and 325(s). These bands also indicate the assigned composition to be correct. It should be noted that only one addition isomer was found although a second isomer, ClCF$_2$CF(OTeF$_5$)CF$_3$, is theoretically also possible.

The major products of this reaction were CF$_3$CFClCF$_3$, TeF$_5$OCF$_2$CFClCF$_3$, and the oily, nonvolatile liquid, (TeF$_4$O)$_2$ as shown in the following reaction.

$$\text{TeF}_5\text{OCl} + \text{CF}_3\text{CF}=\text{CF}_2 \rightarrow \text{CF}_3\text{CFClCF}_3 + (\text{TeF}_4\text{O})_2 + \text{TeF}_5\text{OCF}_2\text{CFClCF}_3 \quad (\text{VII})$$

These are readily separable from the desired TeF$_5$OCF$_2$CFClCF$_3$ adduct due to their great volatility differences.

From a consideration of the above it can be seen that the present invention provides a novel class of high density fluids and a simple, direct, and effective route for their synthesis.

While this invention has been described with reference to preferred embodiments thereof, it should be understood by those skilled in the art that various alterations and modifications that come within the purview of the appended claims are intended to be included herein.

What is claimed is:

1. A high density, TeF$_5$O— substituted, fluorocarbon fluid having the following structural formula:

TeF$_5$OR$_f$ wherein R$_f$ is a radical selected from the group consisting of —CF$_2$CF$_3$; —CF$_2$CF$_2$Cl; —CFClCF$_3$; —CF$_2$CF$_2$CF$_3$; —CF(CF$_3$)$_2$; —CF$_2$CFClCF$_3$ and

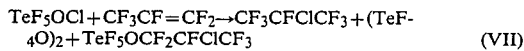
—CFCF$_2$CF$_2$CF$_2$CF$_2$.

2. A high density fluorocarbon fluid in accordance with claim 1 wherein the radical R$_f$ is —CF$_2$CF$_3$.
3. A high density fluorocarbon fluid in accordance with claim 1 wherein the radical R$_f$ is —CF$_2$CF$_2$Cl.
4. A high density fluorocarbon fluid in accordance with claim 1 wherein the radical R$_f$ is —CFClCF$_3$.
5. A high density fluorocarbon fluid in accordance with claim 1 wherein the radical R$_f$ is —CF$_2$CF$_2$CF$_3$.
6. A high density fluorocarbon fluid in accordance with claim 1 wherein the radical R$_f$ is —CF(CF$_3$)$_2$.
7. A high density fluorocarbon fluid in accordance with claim 1 wherein the radical R$_f$ is —CF$_2$CFClCF$_3$.
8. A high density fluorocarbon fluid in accordance with claim 1 wherein the radical R$_f$ is

—CFCF$_2$CF$_2$CF$_2$CF$_2$.

9. A method for synthesizing a pentafluorotellurim oxide fluorocarbon which comprises the steps of:
    (A) cooling an evacuated reaction chamber to a subambient temperature;
    (B) successively condensing (1) a pentafluorotellurium hypohalite and (2) an ethylenically unsaturated, abphatic or acyclic, straight or branch-chained fluorocarbon having from 2 to 5 carbon atoms into said cooled reaction chamber;
    (C) raising the subambient temperature of said reaction chamber to ambient temperature and maintaining said ambient temperature for a period of time, sufficient to effect a reaction between said hypohalite and said fluorocarbon thereby synthesizing a highly dense reaction product;
    (D) fractionally condensing said reaction product successively at a series of temperatures sufficient to produce respectively a (1) less volatile fraction and (2) a more volatile fraction; and
    (E) collecting said less volatile fraction as a pentafluorotellurium oxide fluorocarbon reaction product.

10. A method in accordance with claim 9 wherein said hypohalite is pentafluorotellurium hypofluorite.
11. A method in accordance with claim 9 wherein said hypohalite is pentafluorotellurium hypochlorite.
12. A method in accordance with claim 9 wherein said ethyleneically unsaturated fluorocarbon is tetrafluoroethylene.
13. A method in accordance with claim 9 wherein said ethyleneically unsaturated fluorocarbon is perfluoropropene.
14. A method in accordance with claim 9 wherein said ethyleneically unsaturated fluorocarbon is perfluorocyclopentene.
15. A method in accordance with claim 9 wherein said ethyleneically unsaturated fluorocarbon is chlorotrifluoroethylene.

* * * * *